(12) United States Patent
Ridder et al.

(10) Patent No.: US 6,684,099 B2
(45) Date of Patent: Jan. 27, 2004

(54) APPARATUS AND METHOD FOR REDUCING SPECTRAL COMPLEXITY IN OPTICAL SAMPLING

(75) Inventors: Trent Ridder, Sandia Park, NM (US); John D. Maynard, Albuquerque, NM (US); Russell E. Abbink, Albuquerque, NM (US); Robert D. Johnson, Albuquerque, NM (US)

(73) Assignee: Inlight Solutions, Inc., Albuquerque, NM (US)

( * ) Notice: Subject to any disclaimer, the term of this patent is extended or adjusted under 35 U.S.C. 154(b) by 82 days.

(21) Appl. No.: 10/116,271

(22) Filed: Apr. 4, 2002

(65) Prior Publication Data

US 2003/0191393 A1 Oct. 9, 2003

(51) Int. Cl.[7] .................................................. A61B 5/05
(52) U.S. Cl. ........................ 600/473; 600/476; 600/310; 356/300
(58) Field of Search ................................ 600/473, 476, 600/310; 356/326, 300

(56) References Cited

U.S. PATENT DOCUMENTS

| 4,906,093 | A | * | 3/1990 | Trossarelli | 356/30 |
|---|---|---|---|---|---|
| 5,591,975 | A | * | 1/1997 | Jack et al. | 250/338.5 |
| 5,677,762 | A | * | 10/1997 | Ortyn et al. | 356/39 |
| 5,754,716 | A | * | 5/1998 | Kim et al. | 385/28 |
| 6,198,949 | B1 | * | 3/2001 | Braig et al. | 600/310 |
| 6,332,092 | B1 | * | 12/2001 | Deckert et al. | 600/476 |
| 6,574,490 | B2 | * | 6/2003 | Abbink et al. | 600/316 |

\* cited by examiner

*Primary Examiner*—Dennis Ruhl
*Assistant Examiner*—Barry Pass
(74) *Attorney, Agent, or Firm*—David Crompton; Crompton, Seager & Tufte, LLC

(57) ABSTRACT

An optical sampling subsystem and method that reduces the effect of errors in an optical sampling subsystem when heterogeneously distributed samples are measured in the path of a spectrometer. The optical sampling subsystem is used to collect the non-uniformly distributed radiation exiting the heterogeneous sample and produce a uniform irradiance at its output. The output is then directed into the wavenumber (inverse of wavelength in centimeters) dispersive or modulating device of the spectrometer. The resulting spectra exhibit less spectral complexity arising from components of the sampling subsystem design and the heterogeneous sample, in particular, the effect of wavenumber shift is minimized. Improved quantitative predictions, qualitative analysis and calibration transfer are direct consequences of the reduced spectral complexity.

41 Claims, 11 Drawing Sheets

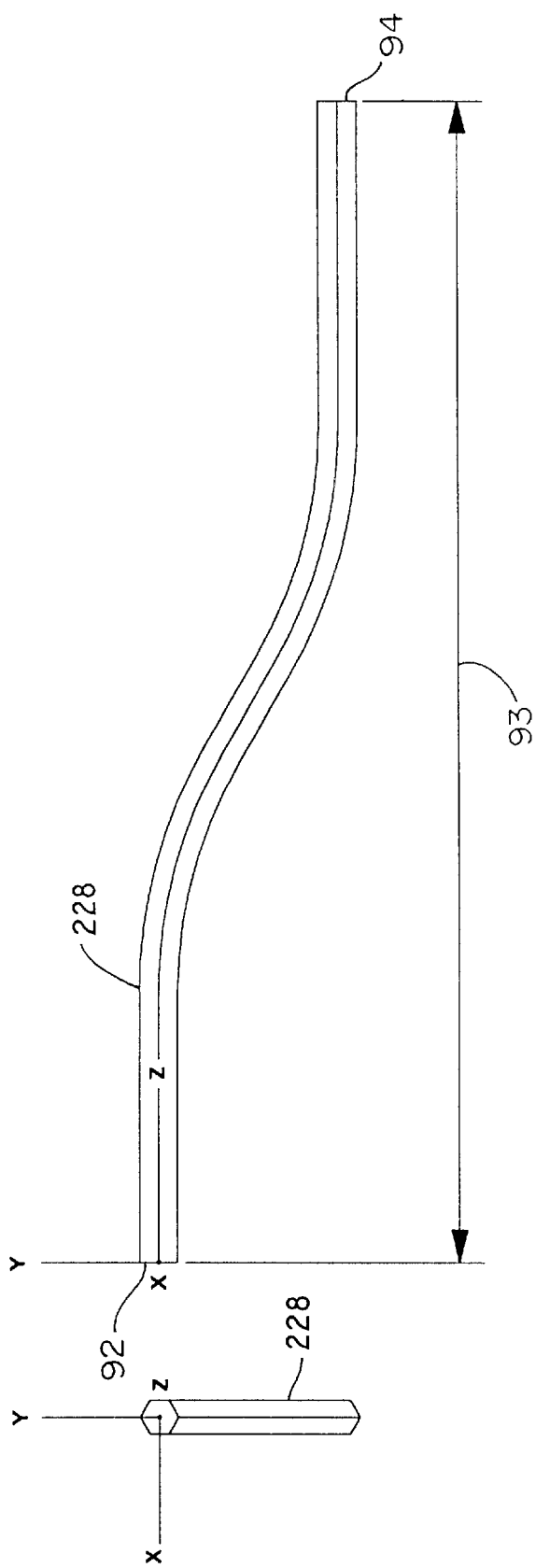

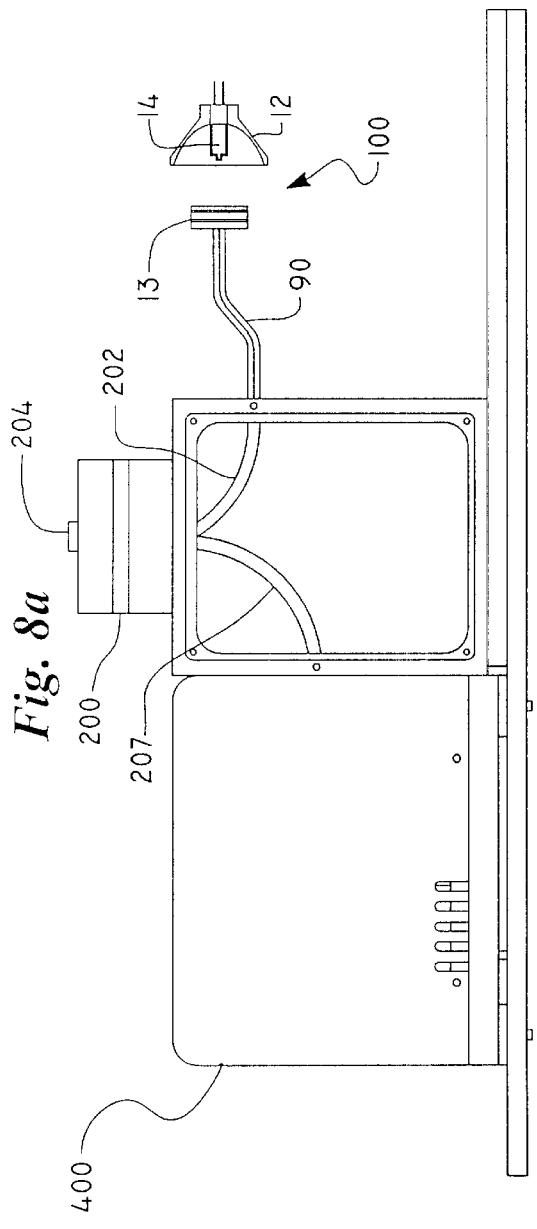
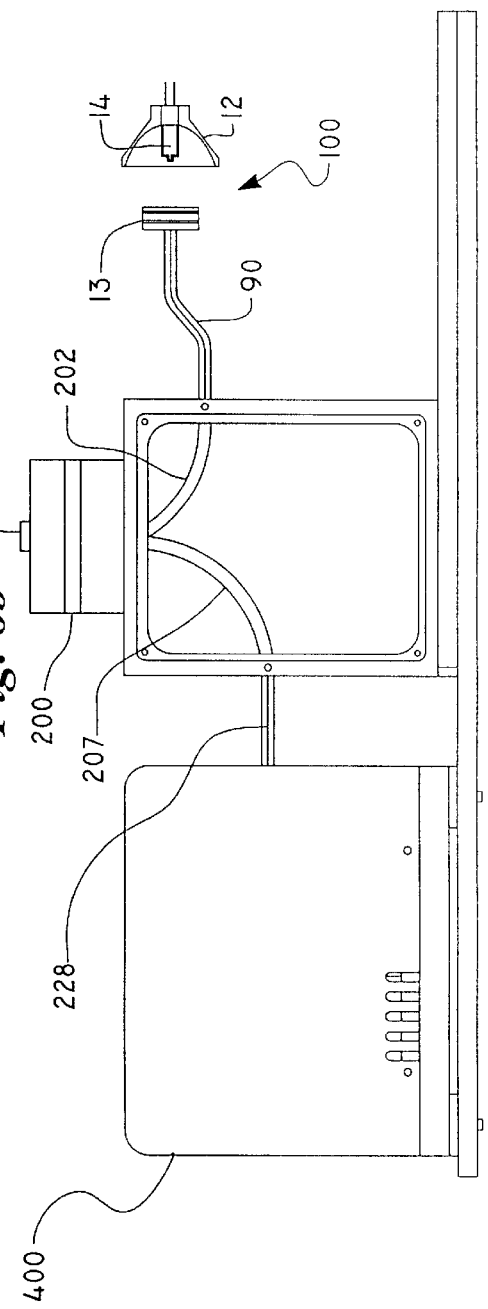

INSERTION #1

INSERTION #2

SUMS OF EACH INSERTION

APPARATUS AND METHOD FOR REDUCING SPECTRAL COMPLEXITY IN OPTICAL SAMPLING

Related Applications

This application is related to U.S. patent application Ser. No. 09/832,585, entitled "System for Non-Invasive Measurement of Glucose in Humans"; U.S. patent application Ser. No. 09/832,586, entitled "Illumination Device and Method for Spectroscopic Analysis"; U.S. patent application Ser. No. 09/832,631, entitled "Encoded Variable Filter Spectrometer"; and U.S. patent application Ser. No. 09/832,608, entitled "Optically Similar References Samples and Related Methods for Multivariate Calibration Models Used in Optical Spectroscopy", all filed on Apr. 11, 2001, and assigned to the assignee of the present application. The disclosure of each of these related applications is hereby incorporated by reference.

TECHNICAL FIELD

The present invention generally relates to the field of diagnostic spectroscopy, and more specifically, to an optical sampling subsystem that reduces the spectral complexity of light exiting a heterogeneous sample and collected by a plurality of fiber optics. The present invention increases the signal-to-noise ratio while compensating for spectral consistency and quantitative performance by providing means for creating a generally uniform radiance at the input of a wavelength dispersive or modulating device.

BACKGROUND OF THE INVENTION

Spectral data arising from spectroscopic analysis provides practitioners with a wealth of detailed information about the identity, structure, concentration or constituents of samples. Spectral data derives from the detected and recorded energy change of a molecule through the emission or absorption of a photon.

In particular, practitioners focus upon a molecule's vibration. Atoms within a molecular species vibrate back and forth about an average distance. Absorption of light by an atom at an appropriate energy causes the atoms to become excited, elevating the atom to a higher vibration level. The excitation of the atoms to an excited state occurs only at certain discrete energy levels, which are characteristic for that particular molecule. Infrared absorption spectroscopy is particularly useful for performing this type of analysis. In absorption spectroscopy, the net absorption of incident radiation at various wavelengths is measured.

Radiation passing through a sample is attenuated depending upon the pathlength traveled by the radiation and the strength of absorptions at various individual wavelengths for constituents within that particular sample. Recording and mapping the relative strength of the absorption versus wavelength results in a unique. absorption "fingerprint" for that particular sample.

One application area for multivariate quantitative spectroscopy is the measurement of tissue attributes or analytes noninvasively. A specific application is the measurement of glucose noninvasively for subjects with diabetes or subjects to be screened for diabetes. Other analytes or attributes of tissue can be measured such as alcohol, urea or the presence of cancer-related abnormalities. All of these applications are difficult due to the complexity of the tissue, a turbid media, and the small size of the analyte or attribute signal. For the measurement of analytes with small concentrations in turbid media, spectroscopic variances that overlap with the absorbance spectrum of the analyte of interest or give the appearance of absorbance at a critical wavenumber have been found to significantly affect the measurement. Spectroscopic interferences can include any spectroscopic variances unrelated to the analyte of interest but present during calibration development or during the measurement. Spectral interferences that overlap with or appear similar to the analyte of interest by showing variation in absorbance at a critical wavenumber, that is not actually due to variation in the analyte or attribute, lead to decreased accuracy of measurement.

In any spectroscopic system, a sampling subsystem must be utilized to introduce light into the sample under analysis, such as tissue, and to collect at least a portion of the light that is not absorbed by the sample to direct this diffusely reflected light to a spectrometer for analysis. The design of the sampling subsystem has been found to introduce variance in the analysis that is not associated with the analyte or attribute under analysis. To achieve accurate analysis, sampling subsystem variances must be reduced or a chemometric model that is insensitive to these variances must be developed. Modeling for sampling subsystem variances increases the complexity of any model, and therefore it is preferred to reduce or eliminate the effects of as many sampling subsystem variances as possible. As disclosed herein, the present invention includes a sampling subsystem design that reduces or eliminates the effects of sampling subsystem variance by reducing the complexity of the spectral analysis of the non-absorbed light collected from a sample after interaction therewith.

SUMMARY OF THE INVENTION

The present invention is directed to an optical sampling subsystem, preferably used for optically sampling tissue. The purpose of the subsystem is to introduce radiation generated by an illumination subsystem into the tissue of a subject or other sample and to collect at least a portion of the light or radiation that has interacted with the tissue or sample and has not been absorbed by the tissue. The subsystem transmits that light or radiation to a spectrometer subsystem for measurement. In particular, the optical sampling subsystem of the present invention reduces the effect of variances introduced by the optical subsystem which would result in less accurate analyte measurement or a more complex model to account for such variances. In preferred embodiments, the optical subsystem reduces spectral complexity of the light exiting the heterogeneous sample and collected by a plurality of optical fibers. The invention, in preferred embodiments, includes means for creating a generally uniform radiance at the input of a wavelength dispersive or modulating device within the spectrometer subsystem.

The means for creating a generally uniform radiance at the input of the wavelength dispersive or modulating device is preferably a radiation homogenizer which is used in combination with preferred optical inputs and optical outputs. A preferred optical ouput includes a plurality of optical fibers bundled in a spaced geometric pattern that collects the most light possible from the illumination subsystem after sample interaction in order to maximize the signal-to-noise ratio achieved by the subsystem. The combination of optical input and optical output devices disclosed herein and the means for creating a generally uniform radiance at the input of the wavelength dispersive or modulating device reduces the spectral complexity arising from photometric errors introduced by the heterogeneous sample and also reduces instrument dependent X-axis shift in order to reduce the complexity of the spectra analyzed by the multivariate calibration model used to determine a property or analyte concentration.

In preferred embodiments of the present invention, the sampling subsystem is incorporated into a spectroscopic system for determining a property of a heterogeneous sample. The apparatus preferably includes a light source that generates light with the light source optically coupled to a sampling means for transmitting at least a portion of the generated light to tissue and collecting at least a portion of the light modified by interaction with the tissue. The sampling means preferably includes a sample head for receiving a sample and a plurality of receiver optical fibers which have input ends and output ends. The input ends are disposed in the sample head for collecting at least a portion of the light modified by the tissue, while the output ends are optically coupled to an input end of a radiation homogenizer. The output from the radiation homogenizer is transferred to a spectrometer through optical coupling with the output end of the receiver optical fibers. The spectrometer includes means for processing the optical information to determine a property of the sample.

In preferred embodiments, the illumination subsystem generates near-infrared light including at least one wavelength indicative of the property of interest in human tissue. The spectrometer is preferably an FTIR spectrometer and further preferably includes a data acquisition subsystem which receives the electrical representation of the interferogram from the FTIR spectrometer. The data acquisition subsystem preferably includes means for amplifying and filtering the electrical representation and converting a resulting electrical signal to its digital representation. Finally, the system preferably includes a computing subsystem for receiving the digital representation which further includes a multivariate algorithm for calculating the property in human tissue.

In a preferred method for spectroscopic analysis, the above system is provided and radiation is emitted from the radiation source emitter and illuminates the sample with such radiation. At least a portion of the radiation is collected after interaction with the sample by a plurality of optical fibers. The output from the optical fibers is then homogenized with subsequent transfer to a spectrometer and detector for measuring the analyte concentration within the sample source.

BRIEF DESCRIPTION OF THE DRAWINGS

FIG. 7A is a end plan view of a preferred light pipe;

FIG. 7B is a side plan view of the preferred light pipe of FIG. 7A;

FIG. 8A is a schematic representation of a test apparatus used to determine the source and effects of variances introduced by a preferred sampling subsystem;

FIG. 8B is a schematic representation of the test apparatus of FIG. 8A, including one embodiment of the present invention, used to measure improvements achieved by homogenizing the output light;

DETAILED DESCRIPTION

An ideal spectrophotometer system would use a perfectly efficient and stable point source in optimal alignment with optical components that contribute no aberrations or variances and a detector that is perfectly efficient, noise-free, and captures all photons emitted by the source. If no sample were present, a spectrum obtained from such an instrument system would be exactly representative of the source's emission. With the introduction of an absorbing sample into the optical path, the absolute transmission spectrum of the sample could be easily determined, because there would be no photometric errors or variances in the spectrum induced by the spectrophotometer system. Consequently, the spectrophotometer would not contribute any error or complications in qualitative or quantitative analysis.

Because ideal elements for an instrument do not exist, practical instrument designs are forced to introduce variances or photometric errors. One subsystem of a spectrophotometer system which will introduce variances or photometric errors is the optical sampling subsystem. The significance of these variances are believed not to have been understood in most applications. It has been found, as disclosed herein, that sampling subsystem variances can lead to unacceptable errors in analysis for spectroscopic analysis of a heterogeneous sample such as tissue. The errors have been found to be more pronounced when the subsystem is designed to maximize light throughput so that light exiting the tissue after interaction and collected for analysis is sufficient to achieve an adequate signal-to-noise ratio. The present invention provides for an optical sampling subsystem that allows for the reduction or elimination of the effects of photometric errors or variances induced by the subsystem design, which is preferably used to analyze heterogeneous samples. Of particular importance is the subsystem's design to eliminate or reduce photometric errors from the high light throughput in a heterogeneous sample and from wavenumber axis shift (frequency domain equivalent of wavelength axis shift).

Figure 1:
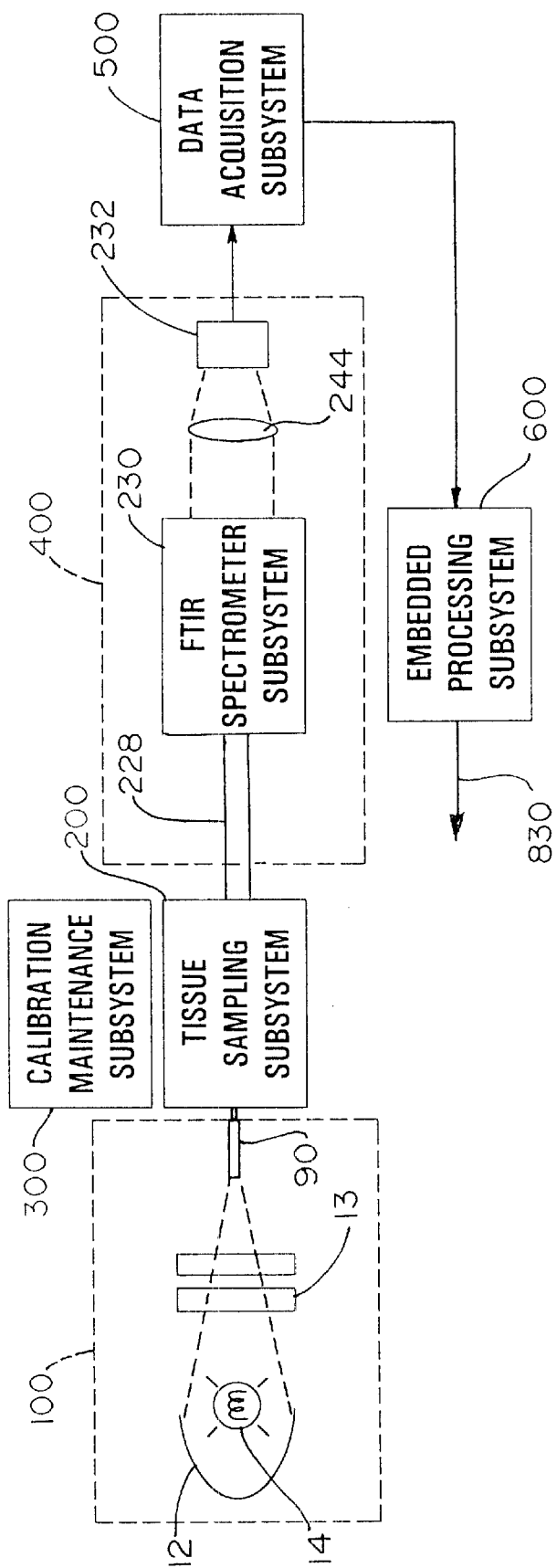
FIG. 1 is a schematic depiction of a non-invasive spectrometer system.

A preferred overall spectroscopic system is first presented, followed by specifics of a preferred optical sampling subsystem incorporated therein. Finally, experimental data is presented that details some of the variances introduced by a sampling subsystem and how the present invention reduces or eliminates the effects of these variances. Referring now to FIG. 1, a non-invasive spectroscopic system used in preferred embodiments is depicted in schematic view. The overall system includes six subsystems. The subsystems include an illumination subsystem 100, a tissue sampling subsystem 200, a calibration maintenance subsystem 300, an FTIR spectrometer subsystem 400, a data acquisition subsystem 500 and an embedded processing subsystem 600. The subsystems have been designed and carefully integrated in order to ensure that the net analyte signal-to-noise ratio is preserved to the maximum amount. The net analyte signal is the portion of the near-infrared spectrum that is specific for determining the concentration of the analyte of interest because it varies orthogonally to other sources of spectral variance. The net analyte signal-to-noise ratio is directly related to the accuracy and precision of the non-invasive measurement of any desired analyte by quantitative near-infrared spectroscopy with the present invention.

The subsystems provide reproducible and preferably uniform radiance of the tissue, low tissue sampling error, depth targeting of the analyte-bearing layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. Each of these factors is optimized to maximize the net analyte signal-to-noise ratio which results in clinically relevant levels of analyte prediction accuracy for diagnosis or therapy. Each of the subsystems is discussed below in summary. However, the present invention is directed to improvements in the tissue sampling subsystem 200 which are described in detail and to the use of the improved tissue sampling subsystem in combination with the other disclosed subsystems. Details of the other subsystems are included in U.S. patent application Ser. No. 09/832,585, entitled "System for Non-Invasive Measurement of Glucose in Humans", and incorporated herein by reference.

Figure 2:
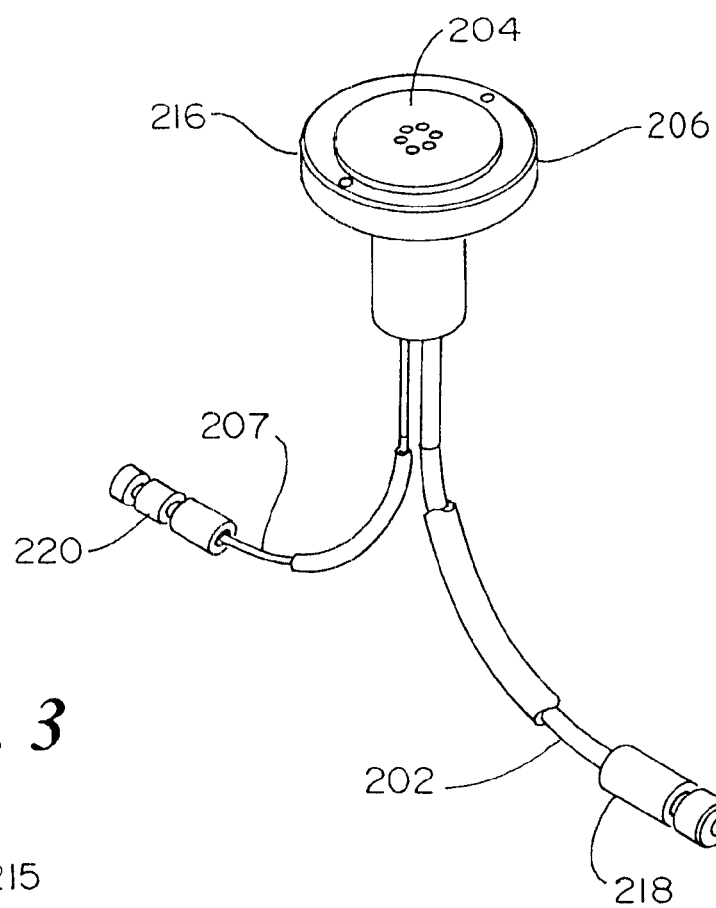
FIG. 2 is a perspective view of elements of a tissue sampling subsystem.
Figure 3:
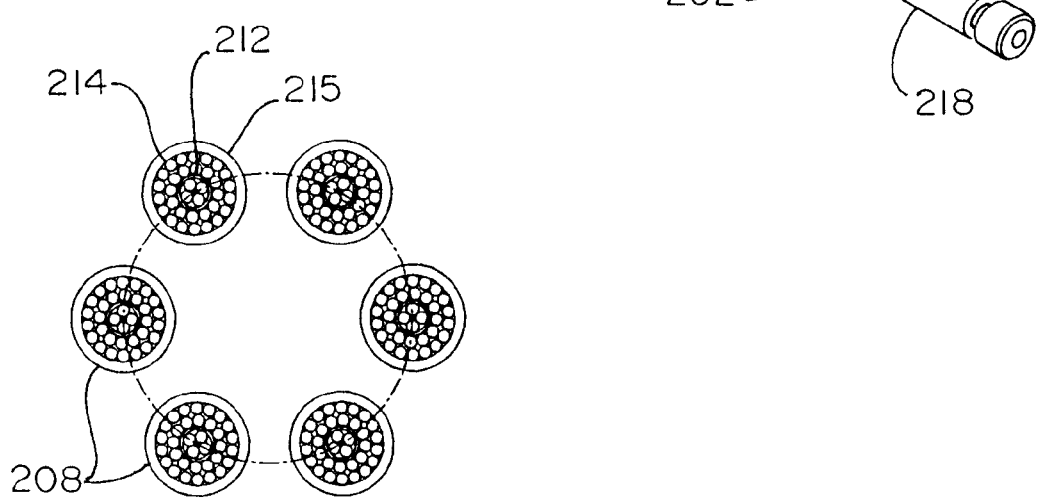
FIG. 3 is a plan view of the sampling surface of the tissue sampling subsystem of FIG. 2 showing an arrangement of illumination and receiver optical fiber ends.
Figure 4:
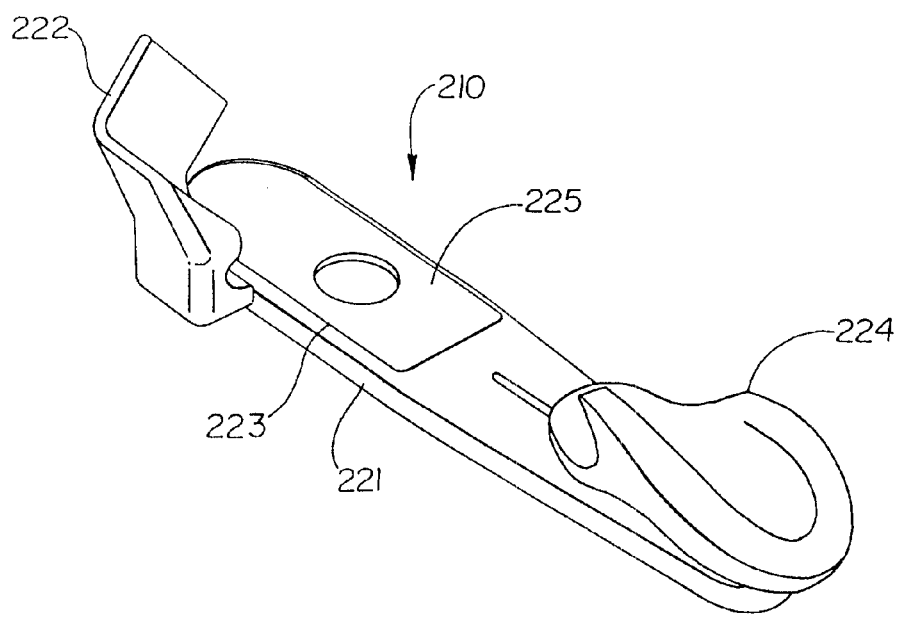
FIG. 4 is a perspective view of an ergonomic apparatus for holding the sampling surface and positioning a tissue surface thereon.

The purpose of the tissue sampling subsystem 200 is to introduce radiation generated by the illumination subsystem 100 into the tissue of the subject and to collect at least portions of the radiation that are not absorbed by the tissue and send that radiation to the FTIR spectrometer subsystem 400 for measurement. FIGS. 2, 3 and 4 depict elements of a preferred tissue sampling subsystem 200. Referring first to FIG. 2, the tissue sampling subsystem 200 has an optical input 202, a sampling surface 204 which forms a tissue interface 206 that interrogates the tissue or sample and an optical output 207. The subsystem further includes an ergonomic apparatus 210, depicted in FIG. 4, which holds the sampling surface 204 and positions the tissue at the interface 206. In a preferred subsystem, a device that thermostats the tissue interface is included and, in some embodiments, an apparatus which repositions the tissue on the tissue interface in a repetitive fashion is included.

The optical input 202 of the tissue sampling subsystem 200 receives radiation from the illumination subsystem 100 (i.e., light exiting the light pipe 90, in FIG. 1) and transfers that radiation to the tissue interface 206. The optical input may include a bundle of optical fibers that are arranged in a spaced geometric pattern that collects the most light possible from the illumination subsystem. One preferred arrangement is depicted in FIG. 3. The plan view depicts the ends of the input and output fibers in a geometry at the sampling surface including six clusters 208 arranged in a circular pattern. Each cluster includes four central output or receiver fibers 212 which collect diffusely reflected light from the tissue. Around each grouping of four central output fibers 212 is a cylinder of material 215 which ensures about a 100-$\mu$m gap between the edges of the central output fibers 212 and the inner ring of input fibers 214. The 100-$\mu$m gap is important to target analytes such as glucose in the dermis and eliminate specularly reflected light. As shown in FIG. 3, two concentric rings of input fibers 214 are arranged around the cylinder of material 215. As shown in one preferred embodiment, 32 input fibers surround the four output fibers. A high ratio of input-to-output fibers is maintained in preferred embodiments in recognition of loss within the tissue.

All of the clustered input and output fibers are potted into a cluster ferrule which is glued into a sampling head 216. The sampling head 216 includes the sampling surface 204 which is polished flat to allow formation of a good tissue interface. Likewise, the input fibers are clustered into a ferrule 218 connected at the input ends to interface with the illumination subsystem 100. The output ends of the output fibers are clustered into a ferrule 220 for interface with the FTIR spectrometer subsystem 400.

Alternatively, the optical input may not require any fibers and may instead use a combination of light pipes, refractive and/or reflective optics to transfer the maximum amount of input light to the tissue interface. It is important that the input optics of the tissue sampling subsystem collect as much light as possible from the illumination subsystem 100 in order to maximize the SNR achieved by the overall system. In the art, FTIR spectrometer-based non-invasive analyte monitoring systems have been described with the illumination subsystem before the FTIR spectrometer and the tissue sampling subsystem after the FTIR spectrometer. This configuration as described in the art has the disadvantage of limiting the total throughput of the system because the FTIR spectrometer cannot support a large range of angles from the illumination subsystem due to spectral resolution and physical size requirements. In the present invention, the placement of the illumination subsystem 100 and tissue sampling subsystem 200 before the FTIR spectrometer subsystem 400 results in over an order of magnitude improvement in throughput for a given size of FTIR spectrometer because the input to the tissue sampling subsystem 200 is designed to handle the wide range of angles from the illumination subsystem 100 and the small output image size of the tissue sampling subsystem is better matched to the throughput supported by a reasonably sized FTIR spectrometer. The source, sample, FTIR spectrometer, detector (SSFD) configuration for non-invasive analyte monitoring in tissue is a significant improvement over the current art.

The tissue interface is another part of the tissue sampling subsystem. It must irradiate the tissue in a manner that targets the analyte bearing compartments of the tissue and discriminate against light that does not travel a significant distance through those compartments. As stated above, the 100-$\mu$m gap discriminates against light which contains little analyte information. In addition, the tissue interface may need to average over a certain area of the tissue to reduce errors due to the heterogeneous nature of the tissue. The tissue sampling interface should reject specular and short pathlength rays and it must collect the portion of the light that travels the desired pathlength through the tissue with high efficiency in order to maximize the SNR of the system. The tissue sampling interface may employ optical fibers to channel the light from the input to the tissue in a predetermined geometry as discussed above. The optical fibers may be arranged in a pattern that targets certain layers of the tissue that contain good analyte concentration information. The spacing and placement of the input and output or receiver fibers can be arranged in an optimal manner to achieve effective depth targeting. In addition to the use of optical fibers, the tissue sampling interface can use a non-fiber based arrangement that places a pattern of input and output areas on the surface of the tissue when using diffuse reflectance. Proper masking of the non-fiber based tissue sampling interface ensures that the input light travels a minimum distance in the tissue and contains valid glucose or other analyte concentration information.

Finally, the tissue sampling interface may be thermostatted to control the temperature of the tissue in a predetermined fashion. The temperature of the tissue sampling interface is set such that the invention reduces prediction errors due to temperature variation and also such that glucose direction of change can be inferred by the equilibration of the interstitial space with capillary blood glucose levels. In preferred embodiments, the sampling head 216 is heated to between 34° C. and 40° C. in order to thermostat the tissue. This promotes equilibration of analytes between the interstitial fluid and the capillary blood. Further, reference errors are reduced when building a calibration model. These methods are disclosed in commonly assigned U.S. patent application Ser. No. 09/343,800, entitled "Method and Apparatus for Non-Invasive Blood Analyte Measurement with Fluid Compartment Equilibration," the disclosure of which is incorporated herein by reference.

The tissue sampling subsystem generally will employ an ergonomic apparatus or cradle 210 that positions the tissue over the sampling interface 206 in a reproducible manner. A preferred ergonomic apparatus 210 is depicted in FIG. 4. In the case of sampling the underside of the forearm, an ergonomic cradle design is essential to ensure good contact with the sampling interface. The ergonomic cradle 210 includes a base 221 having an opening 223 therethrough. The opening is sized for receiving the sample head 216 therein to position the sampling surface 204 generally coplanar with an upper surface 225 of the base 221. The ergonomic cradle 210 references the elbow and upper arm of the subject via a bracket 222 in conjunction with a float-to-fit handgrip 224 to accurately position the forearm on the tissue sampling interface. Careful attention must be given to the ergonomics of the tissue sampling interface or significant sampling error can result. Errors in sampling the tissue have been found to be a major source of reduced accuracy and precision for the non-invasive measurement of certain analytes such as glucose.

The ergonomic cradle 210 can be a part of the tissue sampling subsystem 200. The cradle is designed such that the forearm of the subject is reliably located over the sample head 216. The bracket 222 forms an elbow rest that sets the proper angle between the upper arm and the sampling head 216, and also serves as a registration point for the arm. The adjustable hand rest 224 is designed to hold the fingers in a relaxed manner. The hand rest position is adjusted for each subject to accommodate different forearm lengths. In preferred embodiments, a lifting mechanism is included which raises and lowers the cradle periodically during sampling to break and reform the tissue interface. Reformation of the interface facilitates reduction of sampling errors due to the rough nature and inhomogeneity of the skin.

In preferred embodiments, the image formed by the output of the tissue sampling subsystem is typically an order of magnitude smaller in size than its input. This input image to output image ratio is necessary to match the throughput supported by the FTIR spectrometer while maximizing the overall system signal to noise ratio. The output of the tissue sampling subsystem 200 transfers the portion of the light not absorbed by the tissue that has traveled an acceptable path through the tissue to the input of the FTIR spectrometer subsystem 400.

Preferred embodiments of the invention are comprised of two parts. The first of these is the specific optical device that is used to collect light from the sample in combination with means to convert heterogeneous output irradiances into homogeneous irradiances. The second component is the location of the optical device in a spectrometer's optical path. While each of these components is discussed separately, the method's embodiments are considered to be any combination of the embodiments of each of the two components or any obvious variations of the irradiance conversion device or obvious variations on the location of the device in a spectrometer.

In preferred embodiments, elements used to collect and transfer light from the sample to the spectrometer include a plurality of clustered collection optical fibers in combination with means for reducing variance introduced by the sampling subsystem design. The means for reducing variance introduced by the sampling subsystem is preferably a radiation homogenizer. It is recognized that a radiation homogenizer can effect both spatial and angular homogenization. In preferred embodiments of the present invention, the radiation homogenizer effects spatial homogenization. Angular homogenization can also be included in the radiation homogenizer design.

Several designs of a radiation homogenizer may be employed to convert the heterogeneous output irradiance to a homogeneous irradiance. While their functionality is similar, they can be generally classified into two separate categories, light pipes and integrating chambers. Light pipes can be thought of as drawn tubes, being solid or hollow, where the input and output ports are nominally of the same size and shape as the cross-sectional area of the tube. Integrating chambers typically have input and output ports smaller than the sides of the chamber, and may or may not be located opposite of one another. Integrating chambers may also be solid or hollow. The surfaces of either category may be specularly and/or diffusely reflective. Diffusely reflecting surfaces can be used to provide a homogeneous angular distribution at the output of the device.

One such embodiment of an apparatus used to create a homogenous irradiance is that of a light pipe. Light pipes may have a three or more surface cross section and may be made solid or hollow with diffusely and/or specularly reflective surfaces. They may be straight or contain one or more bends. A circular cross section is believed undesirable as it would be less efficient in homogenizing the radiation. Solid light pipes are ideally made of an optically transparent material or combination of materials. Radiation enters the light pipe at one end, propagates the length of the light pipe, and exits the opposite end of the pipe, exhibiting the desired homogeneous properties at that point.

For cost considerations, a hollow light pipe is preferably employed. Hollow light pipes may be made of any substrate material suitable to holding the desired form and shape of the design. Plastic, glass or metal are examples of acceptable materials that may be used to form a hollow light pipe. In addition, hollow light pipes may be coated with a reflective material or left uncoated, and can be polished to create a specularly reflecting surface or roughened to create a diffusely reflecting surface. Hollow light pipes are similar in function to solid light pipes, wherein radiation enters the hollow light pipe at one end, propagates the length of the light pipe, and exits the opposite end of the pipe, exhibiting the desired homogeneous properties at that point.

Another apparatus that can be used to create a homogenous irradiance is an integrating chamber. Specifically, only non-spherical integrating chambers having four or more sides are considered to give adequate homogeneous properties. Similar to light pipes, the chambers may also be solid or hollow, and each of the sides coated or uncoated. The input and output ports may take on any geometry and are not limited to the cross-sectional shape of any one of the surfaces, as light pipes typically are. Radiation enters one of these ports, designated the input port, and exits the integrating chamber through the other port, designated the output port. The radiation leaving the exit port exhibits the desired homogeneous properties.

The location of the device in a spectrometer's optical path represents a second component of preferred embodiments of the present invention. Preferred sampling devices of the present invention present a spatially homogeneous irradiance to the input of a spectrometer's wavenumber dispersing or modulating device.

Figure 5:
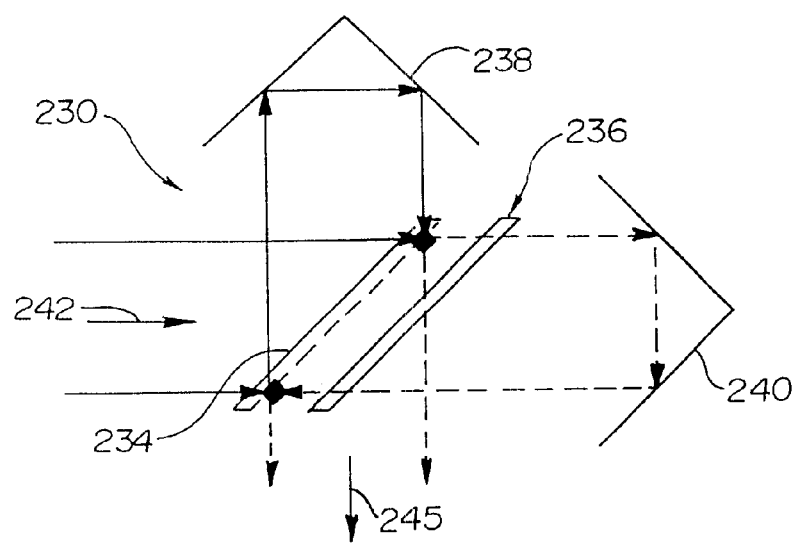
FIG. 5 is a schematic representation of a spectrometer.

As shown in FIG. 1, the FTIR spectrometer subsystem 400 includes a spectrometer 230 that modulates the sufficiently collimated light from the tissue sampling subsystem 200 to create an interferogram which is received by a detector 232. The interferogram spatially encodes the NIR spectrum collected by the tissue sampling subsystem. FIG. 5 schematically depicts one embodiment of an FTIR spectrometer 230 which includes a beamsplitter 234 and compensator optics 236, a fixed retro-reflector 238 and a moving retro-reflector 240. The collimated input light 242 impinges on the beamsplitter optic 234 and is partially reflected and partially transmitted by the coating on the back surface of the beamsplitter 234. The reflected light passes back through the beamsplitter optic 234 and reflects off the fixed retro-reflector 238 and back to the beamsplitter 234. The transmitted light passes through the compensator optic 236 and reflects off the moving retro-reflector 240 and back to the beamsplitter 234. The transmitted and reflected portions of the light recombine at the beamsplitter to create an interference pattern or interferogram. The amount of constructive and/or destructive interference between the transmitted and reflected beams is dependent on the spectral content of the collimated input beam 242 and on the optical path difference between the fixed retro-reflector 238 and the moving retro-reflector 240.

Figure 6:
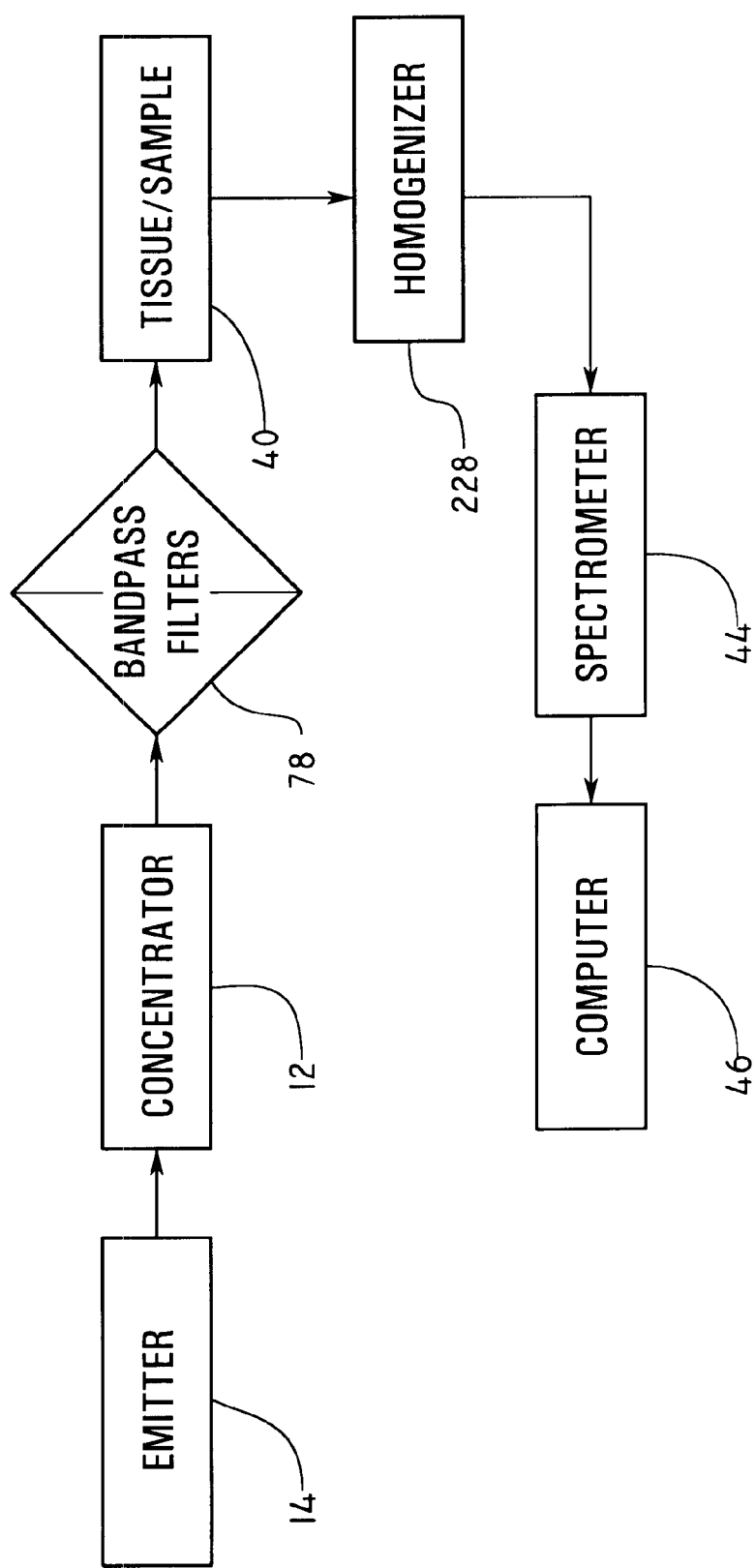
FIG. 6 is a block diagram of a preferred system incorporating a radiation homogenizer.

The sampling subsystem 200 of the present invention overcomes inaccuracies introduced by variances created by the sampling subsystem design. FIG. 6 schematically depicts a simplified system incorporating means for homogenizing the light collected by the collection optical fibers after sample interaction to help achieve clinically relevant analytical results. In most respects, the apparatus diagrammed in FIG. 6 is consistent with those features discussed in detail with respect to FIG. 1, with the clear identification of a radiation homogenizer 228. In a preferred embodiment, the homogenizer 228 is positioned between the sample 40 and the spectrometer 44, as depicted in FIG. 6. At this location, entering radiation is homogenized prior to its distribution upon the spectrometer 44.

The placement of the homogenizer 228 at the above-described location is preferred. However, the system depicted in FIG. 6 is significantly simplified for illustrative purposes. Only certain specific elements within a far more elaborate spectroscopic system are diagrammed. All the elements depicted in FIG. 6, however, are common to a preferred spectroscopic system of the present invention. The elements diagrammed, therefore, are to aid in identification of various aspects of the overall spectroscopic system. Thus, it should be understood that additional elements, such as a collimating lens or other optic, may be positioned between the tissue 40 and spectrometer 44 on either side of the homogenizer 228. However, the homogenizer 228 is placed at a point between the tissue or sample 40 and the spectrometer 44, and in a preferred embodiment, the homogenizer input end abuts the output ends of the receiver fiber optics. This configuration is preferred, as it has been found that light exiting the fiber optic strands exhibits beam divergence due to the arrangement of fibers.

In a preferred embodiment, the radiation homogenizer 228 is a light pipe. FIGS. 7A and 7B show a end plan view and a side detail plan view of a light pipe 228 of the present invention. Light pipe 228 is generally fabricated from a metallic, glass (amorphous), crystalline, polymeric, or other material, or any combination thereof. Physically, the light pipe 228 comprises a proximal end 92, a distal end 94, and a length 96 therebetween. The length of a light pipe 228, for this application, is measured by drawing a straight line from the proximal end 92 to the distal end 94 of the light pipe. Thus, the same segment of light pipe 228 may have varying lengths depending upon the shape the segment forms. The length of the segment readily varies with the light pipe's intended application.

In a preferred embodiment as illustrated in FIGS. 7A and 7B, the segment forms an S-shaped light pipe. The S-shaped bend in the light pipe provides angular homogenization of the light, if desired, as it passes through the light pipe. Alternatively, a straight light pipe of the same design can be utilized if only spatial homogenization is desired. It is, however, recognized that angular homogenization can be achieved in other ways. A plurality of bends or a non-S-shaped bend could be used. Further, a straight light pipe could be used provided the interior surface of the light pipe included a diffusely reflective coating over at least a portion of the length. The coating provides angular homogenization as the light travels through the pipe. Alternatively, the interior surface of the light pipe can be modified to include dimples or "microstructures" such as micro-optical diffusers or lenses to accomplish angular homogenization.

The cross-section of the light pipe 228 may also form various shapes. In particular, the cross-section of the light pipe 228 is preferably polygonal in shape to provide spatial homogenization. Polygonal cross-sections include all polygonal forms having three to many sides. Certain polygonal cross-sections are proven to improve spatial homogenization of channeled radiation. For example, a light pipe possessing a hexagonal cross-section the entire length thereof provides improved spatial homogenization when compared to a light pipe with a cylindrical cross-section of the same length.

Additionally, cross-sections throughout the length of the light pipe may vary. As such, the shape and diameter of any cross-section at one point along the length of the light pipe may vary with a second cross-section taken at a second point along the same segment of pipe.

In certain embodiments, the light pipe is of a hollow construction between the two ends. In these embodiments, at least one lumen may run the length of the light pipe. The lumens of hollow light pipes generally possess a reflective characteristic. This reflective characteristic aids in channeling radiation through the length of the light pipe so that the radiation may be emitted at the pipe's distal end. The inner diameter of the lumen may further possess either a smooth, a diffuse or a textured surface. The surface characteristics of the reflective lumen aid in spatially and angularly homogenizing radiation as it passes through the length of the light pipe.

In additional embodiments, the light pipe is of solid construction. The solid core could be cover-plated, coated or clad. Again, a solid construction light pipe generally provides for internal reflection. This internal reflection allows radiation entering the proximal end of the solid light pipe to be channeled through the length of the pipe. The channeled radiation may then be emitted out of the distal end of the pipe without significant loss of radiation intensity.

Another method for creating homogenization is to use an integrating sphere in place of the light pipe. Although common to use an integrating sphere for detection of light, especially from samples that scatter light, integrating spheres have not been used as part of the sampling subsystem when seeking to measure analytes non-invasively. In practice, radiation output from the collection optical fibers could be coupled into the integrating sphere with subsequent illumination of the spectrometer through an exit port. An integrating sphere will result in exceptional homogenization, but the efficiency of this system is significantly less than other embodiments previously specified.

A study was conducted to identify sources of variance in optical sampling subsystems of the present invention, and means for eliminating or reducing the effect of these variances were developed and tested. This work is described below. For descriptive purposes, point sources are used to diagram the origins of variances, such as wavenumber shift in a Fourier transform spectrophotometer. Point sources are believed valid, but simplified, representations of the photometric errors encountered in practical instrumentation because an extended source can be considered an infinite, but continuous, collection of point sources. It is important to note that only one point in the source can coincide with the optical axis of the spectrophotometer, and therefore be in perfect alignment, for any source position. The subsequent examples endeavor to explain the origins of spectral differences associated with optical sampling, which by definition are photometric errors, between aligned and misaligned point sources. The basic examples can then be extended to cover the continuum of point sources that would be encountered with the use of an extended source.

The apparatus assembled for identifying variances associated with a sampling subsystem 200 of preferred embodiments of the present invention, is depicted schematically in FIG. 8A. FIG. 8B depicts the same apparatus as FIG. 8A, with the exception of the addition of a light pipe 228. The apparatus of FIG. 8B was utilized to document improvement achieved by incorporation of the present invention into a sampling subsystem 200. The system of both FIGS. 8A and 8B include an illumination subsystem 100. The illumination subsystem 100 includes a source 14 which is mounted within elliptical reflector 12 to direct light from the source to the sampling subsystem. Light from the source passes through a series of filters 13 and a radiation homogenizer 90 prior to reaching the sampling subsystem 200.

The tissue sampling subsystem 200 used in the experiments was the same as that previously described with respect to FIGS. 2 and 3. The tissue sampling subsystem 200 include a plurality of optical input fibers 202 and a sampling surface 204 which forms a tissue interface 206 that interrogates the tissue or sample. In a preferred system, as depicted in FIGS. 8A and 8B, the sampling subsystem 200 also includes a plurality of receiver optical fibers 207. The input and output optical fibers include a clustered geometry as depicted in FIG. 3. Further, the output ends of the output or receiver fibers are clustered into a ferrule for interface with the FTIR spectrometer subsystem 400. With the system of FIG. 8A, light exiting the output fiber optics 207 is transmitted directly to the FTIR spectrometer subsystem 400, while in the device of FIG. 8B, a radiation homogenizer 90 is placed in abutment with the output ends of the output optical fibers to homogenize the output light and transfer the output light to the spectrometer subsystem 400.

A test was conducted utilizing a standardized polystyrene reference sample on the apparatus of FIG. 8A. In conducting the test on this homogeneous sample, only one of the six clusters of optical fibers were used during each analysis, with the other five bundles masked from the sample. In analyzing the data, it was clear that there was an apparent wavenumber variation in the absorption peaks depending upon which fiber optic bundle was utilized.

Figure 9:
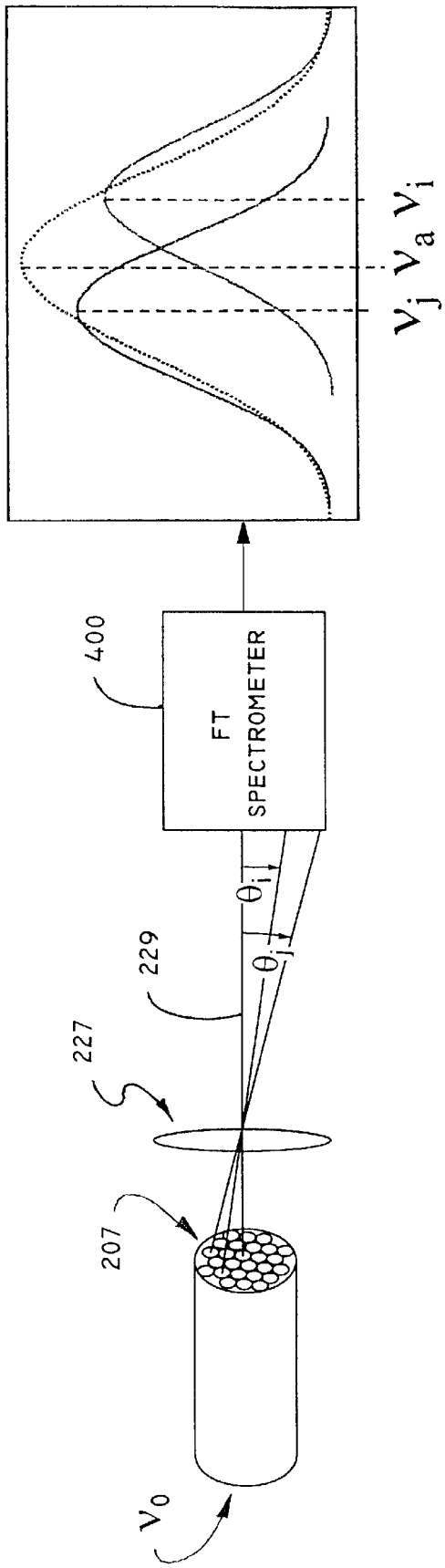
FIG. 9 is a schematic representation of variances introduced by the location of a particular optic fiber in an output cluster.

At least one of the sources of this apparent wavenumber variation is depicted schematically in FIG. 9. Light exiting the output fiber bundles 207 in the system of FIG. 8A is transmitted to the spectrometer subsystem 400 to, for example, a collimating lens 227. As depicted in FIG. 9, depending upon the location of the particular output fiber output bundle, the angle at which the light is transmitted to the spectrometer subsystem will vary. This will further vary depending upon how a particular fiber optic is potted within the ferrule in addition to its geometric location within the overall bundle. As further depicted in FIG. 9, it was found that light traveling along the longitudinal axis 229 into the spectrometer subsystem resulted in a peak depicted by $v_a$ in FIG. 9. Light traveling along an angle $\theta_i$ resulted in an apparent wavenumber variation $v_j$ and light traveling at an angle of $\theta_j$ resulting in an apparent wavenumber $v_j$. This effect was found to be due to the angle at which light entered the interferometer relative to the longitudinal axis and is best understood in reviewing the operation of the interferometer.

Figure 10:
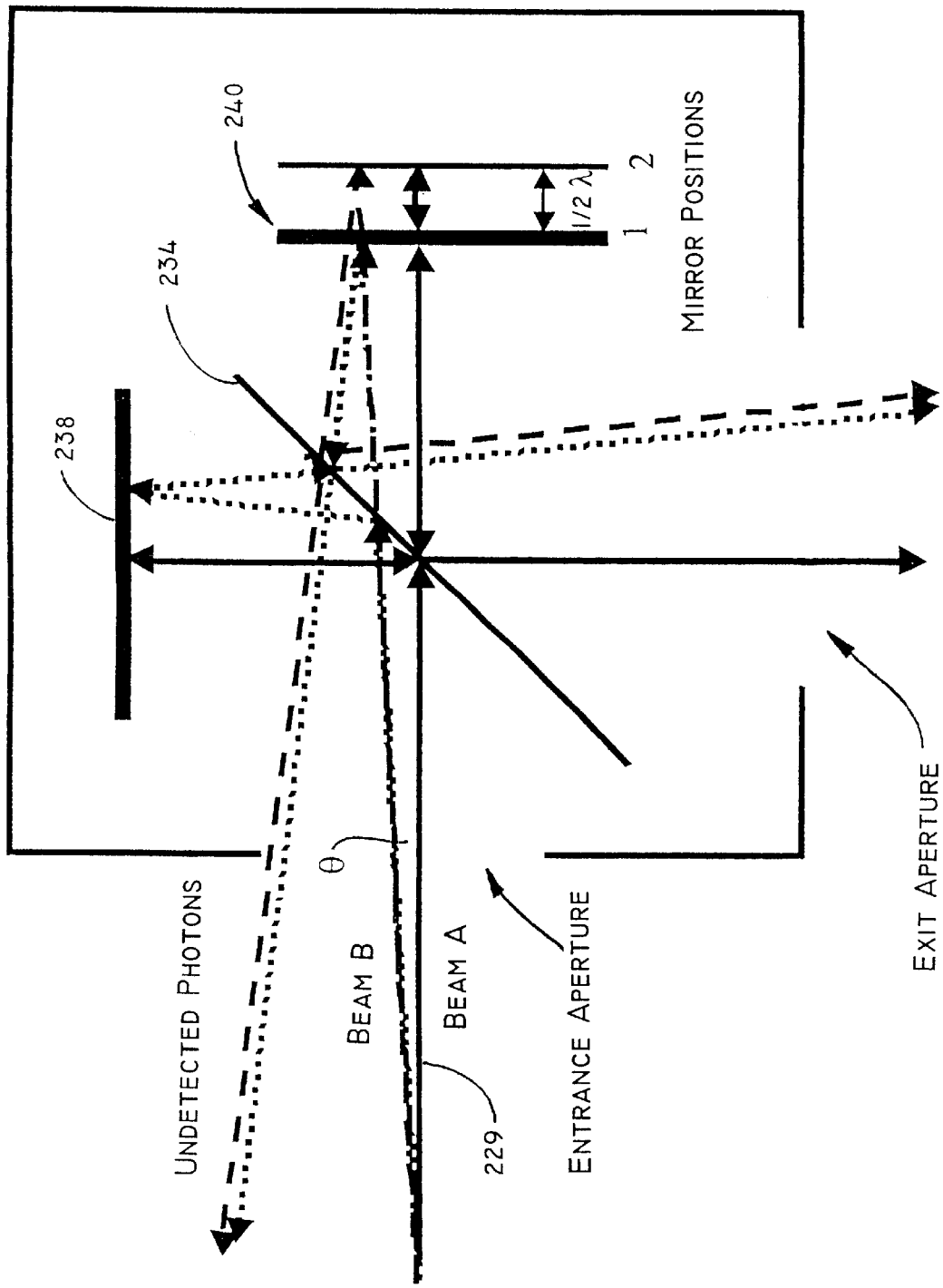
FIG. 10 is a diagram depicting the operation of a basic interferometer receiving beams at varying angles which lead to a perceived wavenumber shift.

FIG. 10 is a diagram that shows the basic components of a Michelson interferometer. Beam A is a perfectly narrow ray of monochromatic light that is aligned with the interferometer's optical axis 229. Upon the introduction of beam A into the interferometer, the beamsplitter 234 transmits 50% of the ray's intensity, while reflecting the remaining 50%. The reflected portion of the ray is directed to the fixed mirror 238 and then redirected back to the beamsplitter 234. The transmitted portion of the ray from the beamsplitter 234 is directed to a moving mirror 240, which in turn reflects the light back to the beamsplitter 234. The separated beams meet at the beamsplitter 234 and interact with each other in a process called interference. Depending on the position of the moving mirror and the wavelength of the monochromatic beam, the observed interference can be either constructive or destructive.

FIG. 10 shows two possible positions for the moving mirror. In position 1, the distance between each mirror and the beamsplitter is identical. This means that photons traveling along either path will have traveled exactly the same distance, and will therefore be in phase with each other when they meet at the beamsplitter. In this case, their interaction will result in constructive interference. In position 2, the moving mirror has been moved exactly one-half of a wavelength of the beam's photons. Therefore, the difference in path length between the fixed mirror photons and moving mirror photons is exactly 1 wavelength. Again, the photons from the two paths will be in phase and constructively interfere. However, if the moving mirror were one-fourth of a wavelength from position 1, the difference in path length would be one-half of a wavelength and the photons from the two paths would be exactly out of phase with each other upon recombination at the beamsplitter. In this case, completely destructive interference would result. For all moving mirror positions that do not result in a path length difference corresponding to an integral number of wavelengths, some amount of destructive interference will occur. The relationship of observed intensity versus a continuous range of mirror positions is called an interferogram.

Beam B in FIG. 10 is also a monochromatic ray with photons of the same wavelength as beam A. The only difference is that the beam is misaligned with the interferometer's optical axis by an angle, θ. For beam B, when the moving mirror is in position 1, constructive interference will result because the path lengths of the photons from the fixed and moving mirrors are identical. In other words, when the mirror is in position 1, constructive interference is observed regardless of the value of θ. When the moving mirror is in position 2, however, there is a path length difference between the photons of beam A and beam B that is dependent on the angle, θ, between the beams. The relationship between θ and the path length difference is given by equation 1.

$$X = \frac{2l}{\cos(\theta)} - 2l \quad (1)$$

where l is the distance the moving mirror is from position 1, θ is the angle between the two beams, and X is the path length difference. Examination of equation 1 indicates that for any combination of l and θ that results in a non-zero value for X, there will be a difference in the interference pattern between the two beams. When Fourier transformed, this difference in interference patterns results in a perceived wavenumber shift in the spectral domain. The relationship between a given wavenumber and its perceived shift at an angle, θ, is given in equation 2.

$$V_{Apparent} = V_{True} (\cos \theta) \quad (2)$$

Applications of spectroscopy typically involve qualitative and quantitative analysis of unknown samples. An ideal spectrometer would measure the sample's chemical signal with no additional noise or signal imparted by the spectrometer itself. Unfortunately, practical instruments contribute significantly to the measured spectrum. These photometric errors cause deviations from the theoretical relationships between measured signal and chemical and physical properties of the sample. The effects of wavenumber shift on univariate quantitative analysis can be demonstrated with a few simple examples involving a Fourier transform spectrometer. While univariate analysis in Fourier Transform Infrared (FTIR) spectroscopy is uncommon, these examples will be used as the foundation for the explanation of the effects of the errors in multivariate analysis.

In quantitative spectroscopy, the accuracy, precision, and stability of the wavenumber axis are critical factors that determine the quality of results. In univariate quantitative analysis, for example, wavenumber axis shifts result in direct deviations from the Beer-Lambert law, which is given in equation 3.

$$A = \epsilon l c \quad (3)$$

where A is the measured absorbance at a specific wavenumber, ε is a constant that is characteristic of the analyte's ability to absorb light at the specified wavenumber, l is the pathlength of photons through the sample, and c is the concentration of the analyte.

Figure 11A:
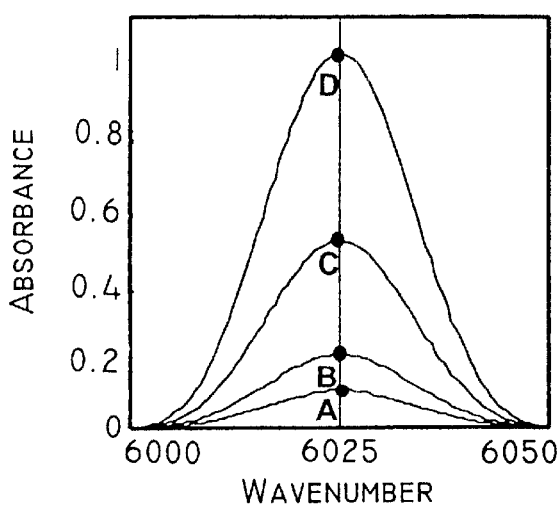
FIGS. 11A–11C graphically depict the effect of wavenumber shift on univariate analysis.
Figure 11B:
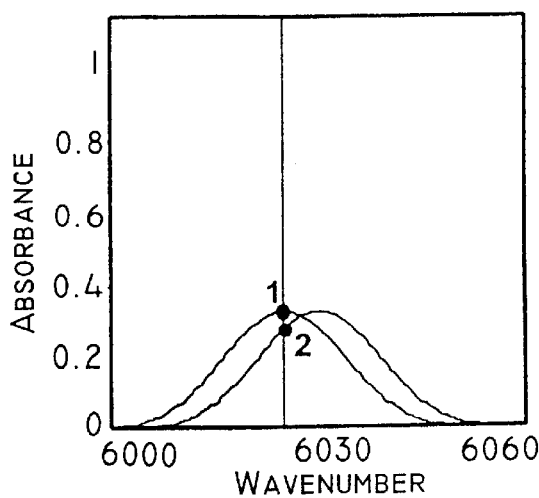
Figure 11C:
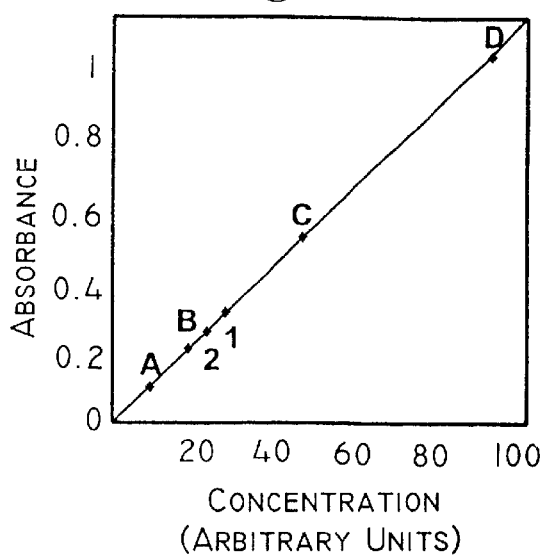

FIGS. 11A–11C gives an example of the error induced by wavenumber axis shifts. FIG. 11A shows an overlay of four simulated absorbance spectra that correspond to different concentrations of an analyte. A calibration curve is obtained by establishing a relationship between the absorbance values at a specified wavenumber and their respective concentrations. The points and line of FIG. 11C show the calibration curve obtained by plotting the absorbance values at 6025 $cm^{-1}$ from the spectra in FIG. 11A versus the respective known concentrations. This calibration curve was then used to predict the concentrations of the simulated spectra shown in FIG. 11B. The two spectra in FIG. 11B have the same peak absorbance values and are assumed to have the same concentration.

The wavenumber location of the absorbance maximum of spectrum 1 in FIG. 11B is 6025 $cm^{-1}$, which is identical to the wavenumber locations of the absorbance maxima for the four spectra used to define the calibration curve. In this case, the concentration prediction of spectrum 1 is accurate. Spectrum 2, however, has the same absorbance maximum value as spectrum 1, but it is located at 6030 $cm^{-1}$. As a result, the absorbance value at 6025 $cm^{-1}$ for spectrum 2, which is the wavenumber location used in prediction, does not correspond to the peak maximum. While the simulated concentration of analyte in spectrum 2 is identical to that of spectrum 1, the predicted concentration of spectrum 2 is significantly lower due to the presence of the wavenumber shift.

In spectroscopy, multivariate methods have largely supplanted univariate methods for qualitative and quantitative analyses. In spectroscopic applications, multivariate methods employ absorbance values from multiple wavenumber locations across a spectrum that can result in quantitative calibrations whose sensitivity to spectral overlap due to the presence of multiple absorbing analytes is reduced. Perhaps the most common multivariate method employed in quantitative analysis is partial least squares (PLS) regression. Consequently, the effects and benefits of this invention towards multivariate qualitative and quantitative applications in spectroscopy will be presented using examples based upon PLS.

The PLS algorithm is used to correlate changes in an analyte's concentration with changes in the spectra of mixtures containing the analyte. The correlation is determined by creating a calibration model that uses a set of spectra obtained from samples of known composition. The result of the calibration is a set of regression coefficients that can be used in conjunction with the spectra of unknown samples to predict the concentrations of the analyte for which the calibration was performed. As with univariate analysis, the presence of photometric errors in the acquired spectra will result in increased prediction errors.

In multivariate analysis employing PLS, wavenumber shifts can result in several undesirable consequences. The observed errors are dependent upon whether the wavenumber shifts occur during the acquisition of calibration spectra or between the acquisition of the calibration and validation spectra. Each of these possibilities will be treated separately.

Wavenumber shifts that occur within the calibration spectra represent an additional dimension of complexity beyond absorption versus wavenumber that must be modeled. The additional complexity in the spectra requires additional factors to be included into the model to account for the wavenumber shifts. The increase in factors will result in a reduction of the net analyte signal, where the net analyte signal is the portion of the spectrum that is specific for the analyte's concentration levels because it is orthogonal to all other sources of spectral variance. The orthogonal nature of the net analyte signal makes it perpendicular to the space defined by any interfering species and as a result, the net analyte signal is uncorrelated to these sources of variance. The net analyte signal-to-noise ratio is directly related to the accuracy and precision of quantitative predictions, which means that a reduced net analyte signal due to the presence of wavenumber shift will result in poorer analyte predictions.

The effects of a wavenumber shift that occurs between calibration and prediction can be explained by considering the regression coefficients and the spectrum to be predicted. Concentration predictions are generated by vector multiplication of the unknown spectrum and the regression coefficients. The output of this multiplication is the concentration prediction. In this process, the regression coefficients generated in the PLS calibration are essentially used to weight the absorbance values in the unknown spectrum. Because each of the regression coefficients corresponds to a specific wavenumber in the spectrum, a wavenumber shift between the calibration and prediction spectra will result in each wavenumber position in the prediction spectrum being weighted by an inappropriate regression coefficient. An increase in prediction errors is a direct result of the weighting errors.

Background correction is a common technique in spectroscopy that is used to remove the instrument response function and environmental effects from analytical spectra. Typically, a background sample contains no analyte and is representative of the instrument's response in the absence of absorbing species. Ideally, background correction would correct for the instrument's response and both instrumental and environmental drift, which would result in stable analytical spectra for qualitative and quantitative analysis. For spectra obtained from samples with a heterogeneously distributed analyte, such as human tissue, in the presence of wavenumber shifts, it has been found that background correction cannot completely remove the instrument's response or instrumental or environmental drift. The following example illustrates this statement.

Figure 12A:
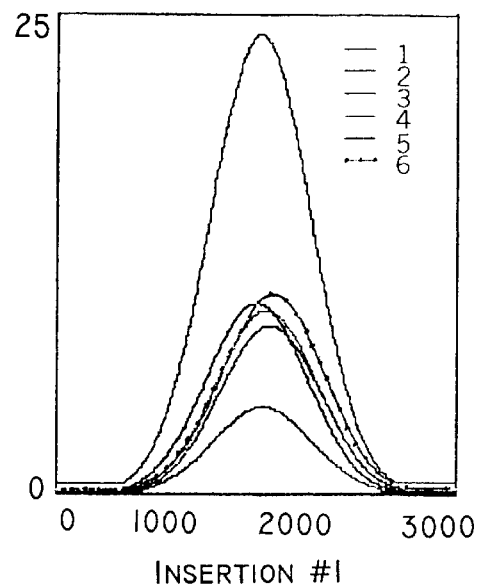
FIGS. 12A–12C graphically depict the effect of wavenumber shift in analyzing a heterogeneous sample.
Figure 12B:
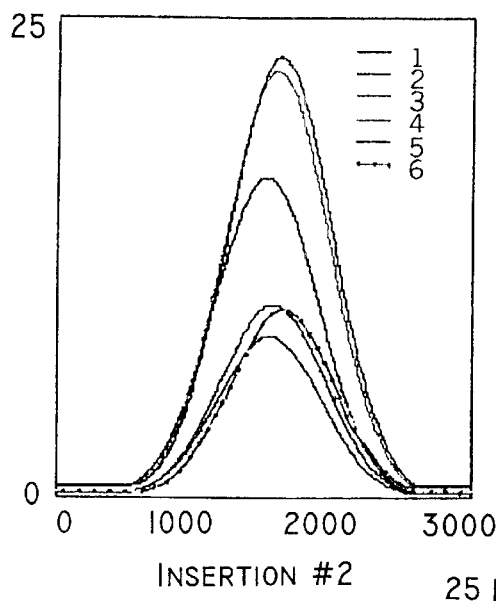
Figure 12C:
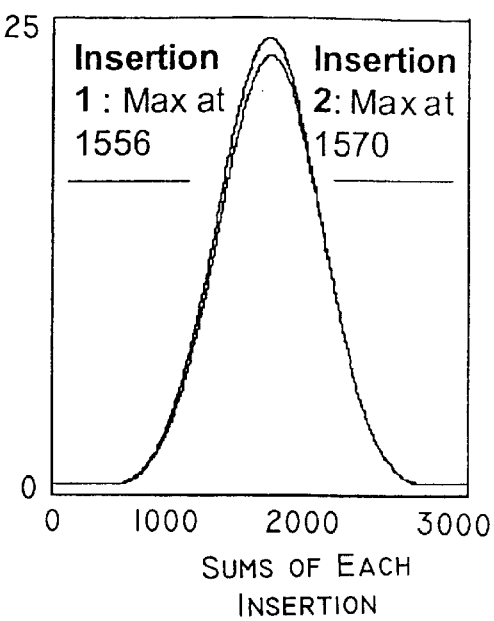

FIGS. 12A–12C are a representation of spectra that might be obtained from six different regions of a heterogeneous sample using an FTIR with a finite source. FIG. 12A represents the six spectra from a single insertion and acquisition of the sample, where an insertion is defined as the placement of the sample on the instrument for spectral acquisition. FIG. 12B represents six spectra of the same heterogeneous sample following reinsertion. The six groups of corresponding spectra in FIGS. 12A and 12B differ in amplitude due to the variation in concentration of analyte each region contains, which result from slight positional changes of the sample with respect to the sampler upon reinsertion. Each region of the source also demonstrates a wavenumber shift due to the differences in angular path through the interferometer. The spectral differences between FIGS. 12A and 12B are due to the redistribution of concentrations across the source regions that occur upon reinsertion of a heterogeneous sample. This effect is also found between individual receiver optical fibers as each receives a quantity of light traveling through different portions of the heterogeneous sample.

In a practical FTIR spectrometer, the spectra corresponding to different regions of the source cannot be independently measured. The spectrum measured by the detector can be considered a mixture of the spectra from different regions of the source. FIG. 12C shows the sums of FIGS. 12A and 12B. The two spectra in FIG. 12C are representative of the signals that would be measured by the detector. The presence of the photometric errors in conjunction with the heterogeneous sample distribution results in a clear difference in absorbance amplitude and wavenumber location of the peak maximum between the two spectra. These spectral differences represent a source of insertion error. It is important to note that neither spectrum can represent the true absorbance amplitude or the true wavenumber position of the feature because both spectra contain photometric errors.

Background correction might be considered to remove these undesired spectral effects. In the case of the two spectra in FIG. 12C, background correction will not remove the insertion errors due to the heterogeneous analyte distribution of the sample because each sample spectrum will be corrected by a background spectrum that does not contain the same spectral effects from wavenumber shift. In other words, background correction will only remove the spectral effects of the photometric errors that were captured equally in the sample and background spectra. As a result, background correction cannot remove the photometric errors due to the reinsertion of samples with a heterogeneous distribution of analyte concentration. It should be noted that a heterogeneous background sample would demonstrate its own insertion error that would increase, rather than remove, the errors due to sample reinsertion.

The invention addresses this problem by reducing or eliminating the differences in photometric errors or variances due to sample subsystem design and between multiple insertions or differences in a particular area of the same heterogeneous sample. The only assumption is that the average amount of analyte observed in each insertion is constant. Consequently, the photometric errors of the heterogeneous sample are consistent in all reinsertions in a manner similar to those of a homogeneous sample. Under these conditions, the two spectra in FIG. 12C would have no insertion error due to these photometric errors.

The effects of the photometric errors in conjunction with heterogeneous samples in calibration transfer can be demonstrated by considering father and daughter instruments of the same design. The instruments will differ only by the variation in quality of the lenses and differences in alignment of the source and detector, which are limited by manufacturing tolerances. The instrumental differences will result in spectra from the father instrument having photometric errors that are different from those of the daughter instrument. As mentioned above, background correction cannot completely remove the effects of these photometric errors for heterogeneous samples. Consequently, a calibration generated from either unaltered sample spectra or background corrected sample spectra from the parent instrument may not be viable to predict either unaltered or background corrected sample spectra from the daughter instrument. The magnitude of the calibration transfer errors caused by wavenumber shift or other sources are directly related to the difference in the spectral shapes of the errors between instruments. In other words, if both instruments demonstrated exactly the same spectral effects from these photometric errors, there would be no associated calibration transfer errors (although there are many other sources of calibration transfer error unrelated to this discussion).

The invention addresses this problem by reducing or eliminating the sample reinsertion error of each instrument. While each instrument will still exhibit a different amount of photometric error relative to the other, the spectral effects of the photometric errors will be more consistent for all spectra obtained on each instrument. Consequently, a simple response correction factor can be used to account for the difference in spectral effects of the photometric errors.

Wavenumber shifts are a consequence of the use of real lenses, an extended source, and a finite sized detector. The magnitude of these errors has been shown to be directly related to the spatial location of photon emission and/or spatial location of the sample in relation to the optical axis of the spectrometer. In order to reduce the effects of these photometric errors, the correlation between the errors and spatial location must be reduced or eliminated. That does not mean to imply that the errors are eliminated, it instead means that all spatial regions are made to have the same magnitude of each photometric error. In this manner, background correction can eliminate the spectral effects of aberrations because an analyte spectrum will contain the same photometric errors as a background spectrum.

The effects of the invention were examined using the fiber optic based testing system of FIG. 8B that is representative of different regions of a finite source. A group of six fiber clusters was illuminated with a 35 W quartz-tungsten-halogen (QTH) lamp. The output portion of the fiber clusters was then directed through an FTIR spectrometer 400. The ideal alignment of the fibers with the spectrometer was determined by locating the position at which maximum energy was detected.

The testing apparatus allowed the selective illumination of each fiber cluster as discussed above. In other words, one fiber cluster could be illuminated while the remaining five were blocked. In this manner, eleven spectra of each fiber were obtained independently of the other fibers. Spectra were also obtained of all six fiber clusters illuminated simultaneously. The spectra when all six fiber clusters were measured simultaneously were used to background correct the spectra for the individual fiber spectra. The testing apparatus was then used to acquire spectra with the invention placed between the fiber outputs and the spectrometer input. The resulting two sets of spectra allow a direct evaluation of the effects of the invention.

Figure 13A:
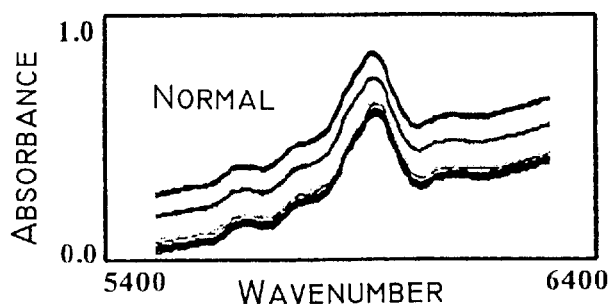
FIGS. 13A–13C graphically depict the benefits of the present invention on a homogenous standard sample.
Figure 13B:
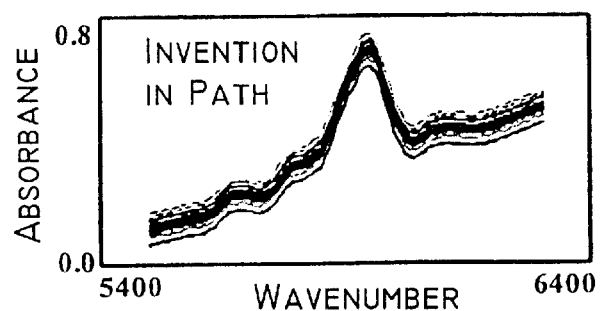
Figure 13C:
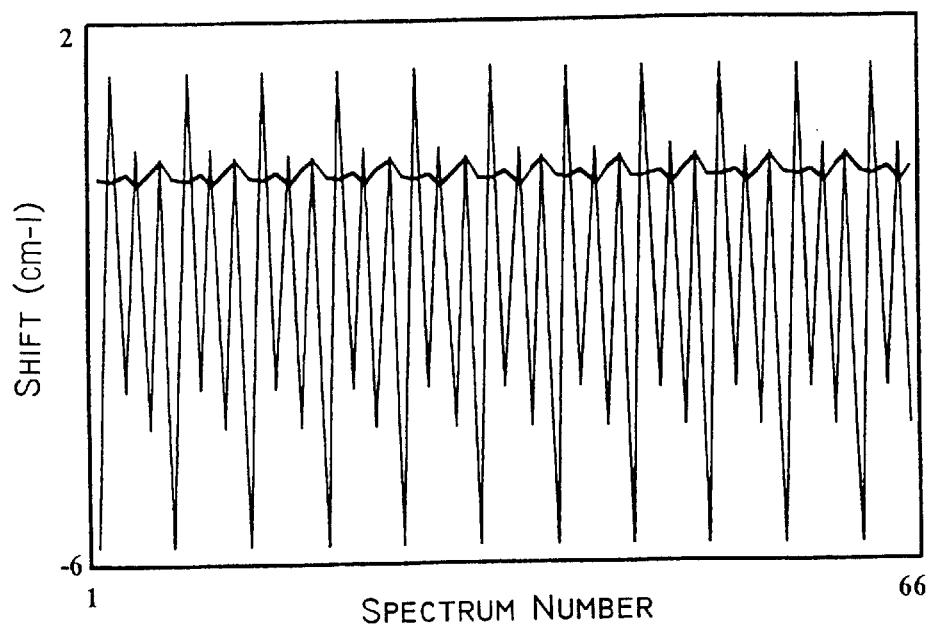

Investigation of the effects of wavenumber shift due to source misalignment were conducted with polystyrene as a reference sample in the optical path between the source and the optical fibers. Polystyrene has several strong absorbance features across the near infrared region, which can be used to determine wavenumber shifts between spectra. For this experiment, an isolated absorbance feature centered at approximately 5950 wavenumbers was used to determine if the spectra from each fiber were shifted relative to the spectra from the other fibers. The shift is calculated by determining the change in the wavenumber location of the absorbance peak relative to a reference spectrum's absorbance peak location. One hundred thirty-two spectra of the optical fibers were obtained from the modified testing system where half of the spectra have the invention in the optical path. FIGS. 13A–13C show the spectra and corresponding spectral shifts. FIG. 13B demonstrates that spectra obtained with the invention in the optical path demonstrate significantly reduced wavenumber shifts in comparison to the spectra obtained in its absence. In both cases, however, there is a distinct pattern to the shifts. The pattern repeats every six spectra, which is representative of the six different optical fiber clusters. It is clear from FIGS. 13A–13C that the range of input angles through the interferometer is significantly smaller when the invention is placed in the optical path. The invention reduces the range of input angles through the interferometer, but it does not insure that the range is centered about zero relative to the optical axis. In other words, while all of the fibers demonstrate similar wavenumber axes, it does not mean that they are accurate relative to the interferometer reference. The alignment of the invention to the optical axis of the interferometer and detector is critical to insure that the wavenumber axis is accurate.

The embodiments of the devices presented in this method belong to a class of optics called nonimaging optics. Nonimaging optics are primarily concerned with the efficient and controlled transfer of radiation, and less concerned with imaging properties. For preferred embodiments of the present invention, the device is designed to create a controlled (uniform) irradiance distribution at its output, which is subsequently directed to the input of a wavelength dispersive or modulating device. It should be noted that the invention could be used in any situation in which any non-uniformities are present, whether they are induced by the source, sample, light collection, or light transfer optics.

The invention is used to collect this non-uniform radiation and produce a uniform irradiance at its output. The spatial uniformity of the output is achieved through a technique called superposition. Through multiple reflections, sub-regions of the non-uniform distribution are superimposed to result in an averaging effect, creating a uniform spatial distribution at the output. Angular uniformity of the output can be achieved with diffusely reflective surfaces in the device or a single or multiple bends in the device. Diffuse surfaces and/or bends result in angular scrambling of the input irradiance.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A sampling subsystem for use in optical analysis of a sample comprising:
   a sample head for receiving the sample for optical analysis including an illumination source optically coupled to the sample head for irradiating the sample and a plurality of optical fibers having input ends and output ends wherein the input ends are mounted in the sample head in spaced relation for receiving at least a portion of the radiation which is diffusely reflected by the sample and transmitting the radiation to the output end of the optical fibers; and
   means for homogenizing at least a portion of the radiation exiting the output end of the optical fibers, the means for homogenizing at least a portion of the radiation disposed between the output end of the optical fiber and an input to a spectrometer wavelength dispersive or modulating device.

2. The sampling subsystem of claim 1, wherein said means for homogenizing said radiation is a light pipe.

3. The sampling subsystem of claim 2, wherein said light pipe has a polygonal cross section.

4. The sampling subsystem of claim 2, wherein said light pipe includes one or more bends to achieve angular homogenization.

5. The sampling subsystem of claim 1, wherein angular homogenization is achieved, at least in part by passing the radiation through a glass diffuser.

6. The sampling subsystem of claim 2, wherein said light pipe includes a diffusely reflective coating on the interior surface thereof.

7. A sampling subsystem for use in optical analysis of a sample comprising:
   a sample head for receiving the sample thereon, the sample head having a plurality of illumination optical fibers, each with an input end and an output end, the input ends receiving radiation and the output ends mounted within the sample head to transmit radiation into the sample, the sample head further including a plurality of receiver optical fibers, each with an input end and an output end, the input ends mounted in spaced relation in the sample head for receiving at least a portion of the radiation that is diffusely reflected from the sample and transmit the radiation to the output ends; and a radiation homogenizer optically coupled to the output ends of the receiver optical fibers disposed between the output ends of the receiver optical fibers and an input to a spectrometer wavelength dispersive or modulating device for homogenizing the radiation prior to measurement.

8. The sampling subsystem of claim 7, wherein said radiation homogenizer is a light pipe.

9. The sampling subsystem of claim 8, wherein said light pipe has a polygonal cross section.

10. The sampling subsystem of claim 8, wherein said light pipe includes one or more bends to achieve angular homogenization.

11. The sampling subsystem of claim 7, wherein angular homogenization is achieved, at least in part, by passing the radiation through a glass diffuser.

12. The sampling subsystem of claim 8, wherein said light pipe includes a diffusely reflective coating on the interior surface thereof.

13. A spectroscopic system for determining property of a heterogeneous sample, the apparatus comprising:

a light source that generates light;

a sampling means for coupling at least a portion of the generated light to tissue and collecting the light modified by the tissue, the sampling means including a sample head for receiving a sample and a plurality of receiver optical fibers including input ends and output ends, the input ends disposed in the sample head for collecting at least a portion of the light modified by the tissue, the output ends optically coupled to an input end of a radiation homogenizer;

a spectrometer optically coupled to an output end of the radiation homogenizer for measuring the optical information of the modified light collected from the tissue; and means for processing the optical information to determine a property of the sample.

14. The spectroscopic system of claim 13, wherein said radiation homogenizer is a light pipe.

15. The spectroscopic system of claim 14, wherein said light pipe has a polygonal cross section.

16. The spectroscopic system of claim 14, wherein said light pipe includes one or more bends to achieve angular homogenization.

17. The spectroscopic system of claim 13, wherein angular homogenization is achieved, at least in part, by passing the radiation through a glass diffuser.

18. The spectroscopic system of claim 14, wherein said light pipe includes a diffusely reflective coating on the interior surface thereof.

19. An apparatus for non-invasively detecting a property of human tissue by near-infrared spectroscopy comprising:

an illumination subsystem which generates near-infrared light including at least one wavelength indicative of the property in human tissue;

a tissue sampling subsystem optically coupled to the illumination subsystem which receives at least a portion of the infrared light, the tissue sampling subsystem including means for irradiating human tissue with at least a portion of the received infrared light and a plurality of optical fibers for collecting at least a portion of the light diffusely reflected from the human tissue, the plurality of optical fibers each including an output end optically coupled to means for spatially and angularly homogenizing the collected light;

an FTIR spectrometer subsystem optically coupled to the means for homogenizing the collected light to receive at least a portion of the homogenized light, the FTIR spectrometer subsystem including a spectrometer that creates an interferogram, the FTIR spectrometer subsystem further including a detector which receives the interferogram and converts the interferogram to an electrical representation;

a data acquisition subsystem which receives the electrical representation of the interferogram, the data acquisition subsystem including means for amplifying and filtering the electrical representation and converting a resulting electrical signal to its digital representation; and a computing subsystem for receiving the digital representation and further including a multivariate algorithm for detecting the property in human tissue.

20. The apparatus of claim 19, wherein said means for homogenizing said radiation is a light pipe.

21. The apparatus of claim 20, wherein said light pipe has a polygonal cross section.

22. The apparatus of claim 20, wherein said light pipe includes one or more bends to achieve angular homogenization.

23. The apparatus of claim 19, wherein angular homogenization is achieved, at least in part by passing the radiation through a glass diffuser.

24. The apparatus of claim 20, wherein said light pipe includes a diffusely reflective coating on the interior surface thereof.

25. A spectroscopic system for measuring analyte concentration in a sample, the system comprising:

a radiation source emitter, the emitter emitting radiation;

a sampler subsystem for transmitting radiation from the source to a sample, the sampler subsystem including a plurality of receiver optical fibers for collecting a portion of the radiation subsequent to interaction with the sample;

a radiation homogenizer disposed to receive the radiation collected by the receiver optical fiber, wherein the homogenizer homogenizes at least a portion of the radiation; and a detector for receiving at least a portion of the homogenized radiation subsequent to interacting with the sample and the radiation homogenizer.

26. The spectroscopic system of claim 25, wherein the sampler subsystem includes a means for channeling the emitted radiation to the sample source.

27. The spectroscopic system of claim 26, wherein the channeling means is at least one fiber optic wire.

28. The spectroscopic system of claim 26, wherein the channeling means is at least one mirror.

29. The spectroscopic system of claim 26, wherein the channeling means is at least one optic lens.

30. The spectroscopic system of claim 25, wherein the radiation homogenizer is a light pipe, wherein the light pipe has a proximal end, a distal end, and a length of material therebetween, the light pipe further having a cross-sectional area.

31. The spectroscopic system of claim 30, wherein the light pipe includes a plurality of bends.

32. The spectroscopic system of claim 31, wherein the plurality of bends form an S-shaped bend.

33. The spectroscopic system of claim 30, wherein the cross-sectional area of the light pipe is polygonal in shape.

34. The spectroscopic system of claim 33, wherein the polygonal shape includes all polygonal forms having three to an infinite number of sides.

35. The spectroscopic system of claim 25, wherein the sample is biological tissue.

36. The spectroscopic system of claim 25, wherein the sample is a human appendage, or a portion thereof.

37. The spectroscopic system of claim 25, wherein the analyte measured is glucose.

38. The spectroscopic system of claim 25, wherein the analyte measured is alcohol.

39. The spectroscopic system of claim 25, wherein the spectroscopic system includes at least one bandpass filter.

40. A method for homogenizing radiation for spectroscopic analysis, the method comprising the steps of:

providing a spectroscopic system, wherein the system comprises a radiation source emitter, a sample having an analyte concentration, a sampler including a plurality of optical fibers for collecting a portion of the radiation after interaction with the sample, a radiation homogenizer, and a radiation detector;

emitting radiation by means of the radiation source emitter;

illuminating the sample with the radiation;

collecting at least a portion of the radiation after interaction with the sample with the plurality of optical fibers;

homogenizing the radiation exiting the plurality of optical fibers; and detecting the analyte concentration within the sample source.

41. The method for homogenizing radiation for spectroscopic analysis of claim 40, wherein the radiation homogenizer is a light pipe.

* * * * *